(12) United States Patent
Brown et al.

(10) Patent No.: US 8,823,246 B2
(45) Date of Patent: Sep. 2, 2014

(54) HIGH FREQUENCY PIEZOCOMPOSITE TRANSDUCER PILLARS

(71) Applicant: FUJIFILM VisualSonics, Inc., Toronto (CA)

(72) Inventors: Jeremy Brown, Halifax (CA); F. Stuart Foster, Toronto (CA); Jianhua Yin, Scarborough (CA)

(73) Assignee: FUJIFILM VisualSonics, Inc., Toronto (CA)

( * ) Notice: Subject to any disclaimer, the term of this patent is extended or adjusted under 35 U.S.C. 154(b) by 0 days.

(21) Appl. No.: 13/676,031

(22) Filed: Nov. 13, 2012

(65) Prior Publication Data

US 2013/0193805 A1 Aug. 1, 2013

Related U.S. Application Data

(63) Continuation of application No. 12/963,096, filed on Dec. 8, 2010, now Pat. No. 8,310,133, which is a continuation of application No. 12/192,816, filed on Aug. 15, 2008, now abandoned.

(60) Provisional application No. 60/983,263, filed on Oct. 29, 2007.

(51) Int. Cl.
*H01L 41/08* (2006.01)
*B06B 1/06* (2006.01)
*A61B 1/06* (2006.01)

(52) U.S. Cl.
CPC . *A61B 1/06* (2013.01); *H01L 41/08* (2013.01); *B06B 1/0622* (2013.01)
USPC .............................. 310/334; 600/459; 600/437

(58) Field of Classification Search
CPC ........................... B06B 1/0622; B06B 1/0629
USPC ................... 310/334, 437, 459; 600/437, 459
See application file for complete search history.

(56) References Cited

U.S. PATENT DOCUMENTS

| 4,398,325 A | 8/1983 | Piaget et al. |
| 5,065,068 A | 11/1991 | Oakley |
| 5,796,207 A | 8/1998 | Safari et al. |

(Continued)

FOREIGN PATENT DOCUMENTS

| JP | 62261300 | 11/1987 |
| WO | WO-2009066184 | 5/2009 |

OTHER PUBLICATIONS

International Searching Authority, International Search Report and Written Opinion, PCT Application PCT/IB2008/003874, mailed Jul. 15, 2009, 8 pages.

(Continued)

*Primary Examiner* — J. San Martin
(74) *Attorney, Agent, or Firm* — Perkins Coie LLP

(57) ABSTRACT

A transducer with triangular cross-sectional shaped pillars is described for suppressing lateral modes within a composite, and a method for producing the same. According to one aspect of the present application, a plurality of triangular cross-sectional shaped pillars extends outwardly from a substrate and form an array of pillars. The resulting array of pillars is configured to suppress the lateral modes of the transducer at higher operating frequencies, such as, at or above 15 MHz, at or above 20 MHz, or at or above 30 MHz.

21 Claims, 8 Drawing Sheets

(56) References Cited

U.S. PATENT DOCUMENTS

| | | | | |
|---|---|---|---|---|
| 6,104,126 | A | * | 8/2000 | Gilmore ................. 310/334 |
| 6,255,761 | B1 | | 7/2001 | Benjamin |
| 6,503,204 | B1 | | 1/2003 | Sumanaweera et al. |
| 6,757,948 | B2 | | 7/2004 | Ptchelintsev et al. |
| 6,806,622 | B1 | | 10/2004 | Schmidt et al. |
| 6,984,284 | B2 | | 1/2006 | Yin et al. |
| 7,377,900 | B2 | | 5/2008 | Vitek et al. |
| 7,489,066 | B2 | | 2/2009 | Scott et al. |
| 7,518,290 | B2 | | 4/2009 | Frey |
| 7,758,509 | B2 | * | 7/2010 | Angelsen et al. ........... 600/447 |
| 8,310,133 | B2 | | 11/2012 | Brown et al. |
| 2003/0216646 | A1 | * | 11/2003 | Angelsen et al. ........... 600/437 |
| 2007/0167815 | A1 | | 7/2007 | Jacobsen et al. |
| 2008/0007142 | A1 | | 1/2008 | Toda |
| 2008/0018199 | A1 | | 1/2008 | Trolier-McKinstry et al. |
| 2009/0108708 | A1 | | 4/2009 | Jiang et al. |
| 2009/0108710 | A1 | | 4/2009 | Brown et al. |

OTHER PUBLICATIONS

Brown, J.A. et al. "Fabrication and Performance of High-Frequency Geometrically Focused Composite Transducer with Triangular Pillar Geometry", IEEE 2007 Ultrasonics Symposium, Oct. 28-31, 2007, pp. 80-83.

Reynolds, P. et al. "Resonant Characteristics of Piezoelectric Composites: Analysis of Spurious Modes in Single and Multi-Element Ultrasonic Transducers," IEEE 2002 Ultrasonics Symposium, Oct. 8-11, 2002, pp. 1157-1160.

United States Patent and Trademark Office, Non-Final Office Action, U.S. Appl. No. 12/192,816, mailed Jun. 8, 2010, 9 pages.

United States Patent and Trademark Office, Non-Final Office Action, U.S. Appl. No. 12/963,096, mailed Sep. 27, 2011, 9 pages.

United States Patent and Trademark Office, Notice of Allowance, U.S. Appl. No. 12/963,096, mailed Apr. 24, 2012, 8 pages.

United States Patent and Trademark Office, Notice of Allowance, U.S. Appl. No. 12/963,096, mailed Jul. 11 2012, 7 pages.

* cited by examiner

HIGH FREQUENCY PIEZOCOMPOSITE TRANSDUCER PILLARS

This application claims the benefit of U.S. Provisional Application No. 60/983,263 filed on Oct. 29, 2007, which application is herein incorporated by reference in its entirety.

BACKGROUND OF THE INVENTION

1. Field of the Invention

This invention relates to piezoelectric composites, and more particularly to piezoelectric composites for high-frequency ultrasound applications and methods of manufacturing such composites.

2. Background Art

Typically, high quality medical imaging uses ultrasonic transducers or transducer arrays that posse the properties of good sensitivity and wide frequency bandwidth. Conventional transducers utilizing monolithic piezoelectric material such as, for example, lead zirconate titanate ("PZT"), typically exhibit a large acoustic impedance mismatch between the transducer and the medium under test, such as, for example, water, human tissue, and the like. To overcome this problem, piezoelectric composites that are made of individual small piezoelectric elements, which can be surrounded and isolated by a polymer matrix, such as, for example, epoxy, have been proposed and implemented at low frequencies. These small piezoelectric elements play an increasingly important role in the development of ultrasonic transducers for medical imaging. One commonly used structure of piezoelectric composite consists of small rectangular or square pillars of PZT that are embedded in a host matrix of polymer material. In one example, the height of the pillars normally about one half wavelength at the operating frequency if the backing material is lower in acoustic impedance.

Unfortunately, developing a high-frequency (>15 Hz) ultrasound transducer is also very challenging due to the extremely small pillar dimensions required in order to avoid significant lateral resonances in the piezoelectric composite. Conventionally, the design of piezo-composites is limited by the blade size limit of micro-dicing saws or other conventional apparatuses that are used to cut the bulk piezoelectric into composite pillars. It is very difficult using conventional dice and fill techniques to sufficiently reduce the size/spacing of the composite pillars enough to push the lateral resonances outside the operating bandwidth of a transponder that is configured to operate at high frequencies. For example, to push the first "lamb mode" frequency to about 80 MHz, while still maintaining a volume fraction of piezoelectric above 25%, a kerf width of approximately 6 μm is required (assuming a typical piezoelectric and epoxy filler). What is needed is a high-frequency ultrasound transducer that operatively suppresses these lateral modes within the piezoelectric composite.

In a flintier aspect, a lens is typically used to passively focus high-frequency ultrasound transducers. Developing a suitable acoustic lens, however, can be very challenging because the lens materials commonly used for lower frequency transducers are far too attenuating at frequencies at higher frequencies. Alternatively, the need for an acoustic lens can be avoided by geometrically curving the transducer. This can be accomplished by using a flexible piezo-composite material as the transducer substrate.

SUMMARY

In one aspect, the present application provides a transducer with triangular cross-sectional shaped pillars for suppressing lateral mod within a piezoelectric composite, and a method for producing the same.

A substrate having a longitudinal axis is provided. According to one aspect, a plurality of pillars is formed that extend outwardly from the substrate. In this aspect, the plurality of pillars can be positioned in adjacent rows that extend substantially parallel to the longitudinal axis of the substrate, forming an array of upright pillars. In one embodiment, each pillar can have a triangular cross-sectional shape formed from a part of side walls and a base.

In one aspect, the array of pillars can comprise a plurality of paired pillars. In this aspect, each of the paired pillars comprises a first pillar positioned adjacent to a second pillar such that a base of the first pillar is spaced from and substantially opposes a base of the second pillar. Further, each row of the array of pillars can comprise a plurality of paired pillars that are positioned adjacent each other such that one side wall of the first pillar is spaced from and substantially opposes one side wall of the second pillar. In this embodiment, the triangular pillars and arrangement thereof are configured to operatively suppress the lateral modes of the transducer at higher operating frequencies, such as, at or above 15 MHz, at or above 20 MHz, or at or above 30 MHz.

In another aspect, a method of producing an ultrasonic wave emission pattern at higher operating frequencies, such as, at or above 15 MHz, at or above 20 MHz, or at or above 30 MHz, is provided. In this aspect, an electric signal can be applied to a piezoelectric substrate of a transducer, which has a plurality of triangular cross-sectional shaped pillars extending outwardly therefrom the substrate. The plurality of pillars can be positioned in rows substantially parallel to a longitudinal axis of the substrate to form an array of pillars. In one aspect, the array of pillars can comprised a plurality of paired pillars in which each of the paired pillars comprises a first pillar positioned adjacent to a second pillar such that a base of the first pillar is spaced from and substantially opposes a base of the second pillar. In a further aspect, it is contemplated that each row of the array of pillars can comprise a plurality of paired pillars that are positioned adjacent each other such that a side wall of the first pillar is spaced from and substantially opposes a side wall of the second pillar.

Additional advantages will be set forth in part in the description which follows, and in part will be obvious from the description, or may be learned by practice of the invention. It is to be understood that both the foregoing general description and the following detailed description are exemplary and explanatory only and are not restrictive of the invention.

BRIEF DESCRIPTION OF THE DRAWINGS

These and other features of the preferred embodiments of the invention will become more apparent in the following detailed description in which reference is made to the appended drawings wherein.

DETAILED DESCRIPTION OF THE INVENTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an," and "the" include plural referents unless the context clearly dictates otherwise. Thus, for example, reference to "a pillar" can include two or more such pillars unless the context indicates otherwise.

Ranges can be expressed herein as from "about" one particular value, and/or to "about" another particular value. When such a range expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Figure 1:
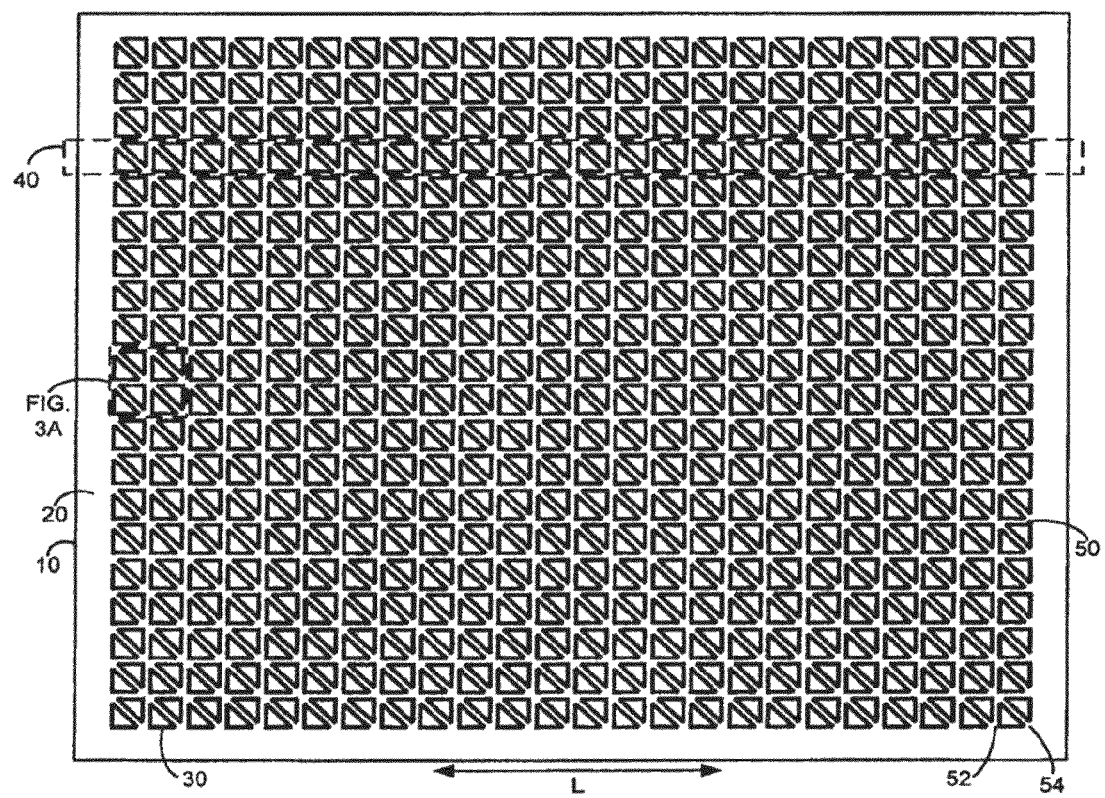
FIG. 1 is a schematic top elevational view of one embodiment of the transducer, showing the surface of a substrate and a plurality of pillars extending therefrom. In this aspect, the pillars have a substantially triangular cross-sectional shape. In one exemplary aspect, it is contemplated that the transducer can have a substantially planar cross-sectional shape. Optionally, it is contemplated that at least a portion of the transducer can have a curved or arcuate cross-sectional shape.
Figure 2A:
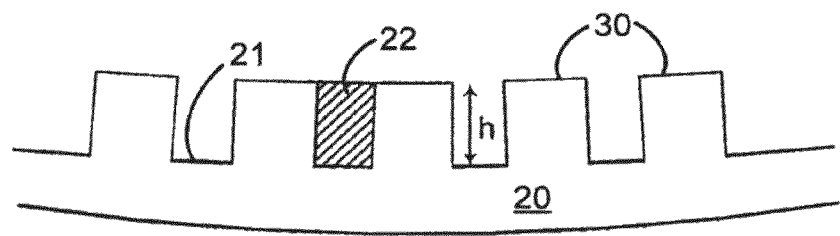
FIG. 2A is a partial cross-sectional view of the transducer of FIG. 1 taken across the longitudinal axis of FIG. 1, showing the substrate of the transducer having an arcuate cross-sectional shape.

As illustrated in FIGS. 1 and 2A, in one embodiment, a transducer 10 of the present application can comprise a substrate 20 and a plurality of pillars 30 tending outwardly from the substrate. The substrate has an upper surface 21 and a longitudinal axis. In one aspect, the substrate can be rigid. In another aspect, however, the substrate can be flexible. In yet another aspect, at least a portion of due substrate of the transducer can have a substantially planar cross-sectional shape. Optionally, it is contemplated that at least a portion of the transducer can have a curved or arcuate cross-sectional shape.

It is contemplated that the substrate can be formed from any desired material having the appropriate electrical and acoustical properties, as commonly known in the art. In one aspect, the substrate 20 can be formed from an electrostrictive material. In another aspect, the substrate can be formed from a piezoelectric material such as, for example and without limitation, lead zirconate titanate. In still another aspect and not meant to be limiting, the substrate can be formed from a single-crystal piezoelectric.

Figure 2B:
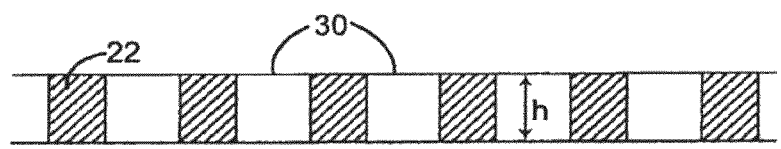
FIG. 2B is a partial cross-sectional view of the transducer of FIG. 2, showing the composite structure after the substrate is ground or lapped of the composite during fabrication and showing the formed pillars extending substantially from top to bottom to form a conventional 1-3 composite.

Referring to FIG. 2B, one skilled in the art will appreciate that it is contemplated that the solid thin layer of monolithic substrate 20 can be conventionally lapped or ground off in a final fabrication step. Thus, in this aspect, when this thin layer of solid substrate 20 is removed, the pillars extend substantially completely through the formed composite from top to bottom. In this example, the composite becomes a conventional 1-3 composite.

Optionally and retorting to FIG. 2A, if the thin strip of substrate 20 is retained at the base of the pillars allows for ease in defining the array electrodes with precision, which allows for ease in operably connecting to the electrodes. Thus, in this aspect, if the thin strip of substrate 20 is retained, the composite formed in a 3-2 composite. One skilled in the art will appreciate that the exemplary 3-2 composite allows for precision definition of array electrodes due to the smooth and continuous bottom surface of the substrate 20, for example and without limitation, by using conventional photolithography techniques and also for ease of connectivity to the electrodes, for example and without limitation, by using conventional wire-bonding techniques. In another aspect, the exemplary substrate can be configured to be flexible such that the composite structure can be curved without fracturing the monolithic layer. Optionally, the monolithic layer can have a thickness that is configured to be thin enough in order to be able to curve the composite without fracturing the monolithic layer. In various examples, it is contemplated that the thickness of the monolithic layer (labelled as "20" in FIG. 2A) can be less than about 15 µm; alternatively less than about 10 µm; and optionally less than about 7 µm.

Figure 3A:
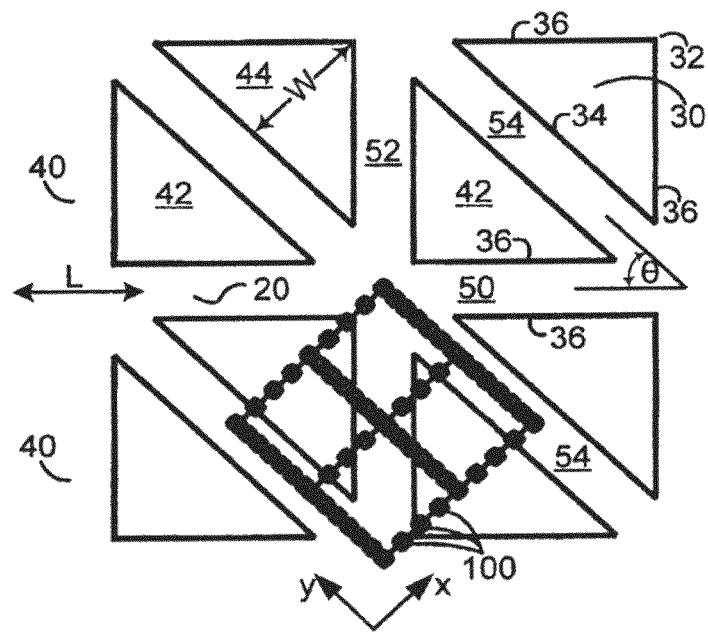
FIG. 3A is an enlarged top elevational view of a portion of the embodiment of the transducer shown in FIG. 1.

The pillars extend outwardly from the substrate 20. In one aspect, and as illustrated in FIGS. 1 and 3A, each pillar can have a triangular cross-sectional shape that has an apex 32, an opposed base 34 baying opposed edges, and a pair of side walls 36 that extend from the apex to the respective edges of the base. In one exemplary aspect, each of the triangular pillars has an isosceles shape. Alternatively, each of the triangular pillars can have a right angle shape. Optionally, it is also contemplated that the pillars can have any generally triangular shape.

The plurality of pillars can be formed from any desired material having the appropriate electrical and acoustical properties, as commonly known in the art. In one aspect, the pillars 30 can be formed from an electrostrictive material. In another aspect, the pillars can be formed from a piezoelectric material such as, for example and without limitation, lead zirconate titanate. In still another aspect, the pillars can be formed from a single-crystal piezoelectric. In one exemplary aspect, the plurality of pillars can be formed from the same material as the substrate 20. Optionally the substrate and the pillars can be formed from a single-crystal piezoelectric.

In a further aspect, it is contemplated that each pillar extends substantially the same height (h) from the upper surface 21 of the substrate 20. Alternatively, it is contemplated that the pillars may vary in height. In various examples, it is contemplated that the height can range from between about 5 μm to 150 μm; alternatively from between about 20 μm to 70 μm; and optionally from between about 40 μm to 50 μm.

In a further aspect, it is contemplated that each pillar can have a width (w) from the base to the apex of the triangular shaped pillar that ranges from between about 40 um to 50 um; alternatively from between about 20 um to 60 um; and optionally from between about 5 um to 70 um.

According to one aspect, the plurality of pillars 30 can form an array of pillars positioned in adjacent rows 40, as illustrated in FIG. 1. In one aspect, each row of the array of pillars can extend substantially parallel to the longitudinal axis of the substrate 20. Referring to FIG. 3A, in another aspect the array of pillars can comprise a plurality of paired pillars. In this exemplary aspect, each of the paired pillars can comprise a first pillar 42 positioned adjacent to a second pillar 44 such that the base 34 of the first pillar is spaced from and substantially opposes the base of the second pillar. Further, in this exemplary aspect, each row 40 of the array of pillars can comprise a plurality of paired pillars that are positioned adjacent each other such that one side all 36 of the first pillar 42 is spaced from and substantially opposes one side wall of the second pillar 44.

As exemplarily illustrated in FIGS. 1 and 3A, in one aspect, the array of pillars can define a plurality of first troughs or kerfs 50 that extend substantially parallel to the longitudinal axis of the substrate 20 and a plurality of second troughs or kerfs 52 that extend substantially transverse to the longitudinal axis of the substrate. Further, the array of pillars can define a plurality of third troughs or kerfs 54 that extend at an acute angle θ relative to the longitudinal axis of the substrate. In a further aspect, it is contemplated that acute angle θ can range from between about 20° to 70°; alternatively from between about 30° to 60% and optionally from between about 40° to 50°. In another aspect, the width of the first trough can be substantially the same as the width of the second trough, and the width of the second trough 52 can be substantially the same as the width of the third trough. Of course, it is also contemplated that the widths of the respective troughs or kerfs can vary in width dimension.

In a further aspect, it is contemplated that each trough or kerf has a width that ranges from between about 1 um to 20 um; alternatively horn between about 5 um to 17 um; and optionally from between about 10 μm to 15 μm, in yet another aspect, it is contemplated that the transponder can be configured such the PZTH5H or single crystal volume fraction ranges from between about 10% to 75%; alternatively from between about 15% to 50%; and optionally from between about 20% to 30.

In yet another aspect, at least a portion of the respective first, second, and third troughs can be at least partially tilled with a fill material 22. The fill material can comprise, for example and without limitation, a polymeric material such as loaded epoxy, polymer micro-spheres, crystal bond, photoresist material and the like, as is customary and standard practice in the manufacture of composite transducers. In one exemplary aspect, the fill material may be SU8 photoresist. Optionally, fill material can comprise a PZT powder. Alternatively, in one aspect, the respective first, second, and third troughs can be left, at least in part, unfilled. One will appreciate that the troughs may not be completely filled or that they may only be filled temporarily as some or the entire trough filling material can removed using conventional methods.

With reference to FIGS. 1-3A and 3C, a transducer can be fabricated to comprise any or all of the features as described above. In one aspect, the substrate 20 can be diced with a dicing saw. A first cutting operation can be performed into the substrate substantially parallel to the longitudinal axis of the substrate so that the plurality of first troughs 50 is defined in the planar upper surface 21 of the substrate. A second cutting operation can be performed into the substrate substantially transverse to the longitudinal axis of the substrate so that the plurality of second troughs 52 is also defined in the planar upper surface of the substrate 20. A third cutting operation can be performed onto the upper surface of the substrate at the acute angle θ relative to the longitudinal axis of the substrate so that the plurality of third troughs 50 are defined in the planar upper surface 21 of the substrate. The cutting operations can be performed so that a plurality of pillars 30 extend outwardly from the substrate 30 as described above, forming an array of pillars.

According to various aspects, the first, second, and third troughs can then be at least partially filled with a fill material, for example and without limitation, comprising SU8 photoresist PZT powder, and the like. Next, the till material can be cured, as is known in the arts. The substrate 20, plurality of pillars and/or fill material can be ground, lapped, or otherwise removed until the desired thickness is achieved. In one exemplary aspect, the thickness of the substrate 20, plurality of pillars and/or fill material can be between 10 and 100 μm. In one exemplary aspect, the thickness of the substrate, plurality of pillars 30 and/or fill material can be about 40-50 μm. In another aspect, the composite structure can have a au material volume fraction of between 10% and 50%. In one exemplary aspect and in consideration of the maintenance of a desirable electromechanical coupling coefficient, the fill material volume fraction can be about 20% to 30%.

According to other aspects, at least a portion of the substrate 20, plurality of pillars and/or fill material can be formed into a spherical geometry having a radius of curvature between 1 and 50 mm. In another aspect, the substrate, plurality or pillars 30 and/or fill material can be formed into a spherical geometry having a radius of curvature of about 9 mm. The substrate, plurality of pillars and/or fill material can then be mounted into an SMA connector using a conductive backing epoxy, as commonly known in the arts. Finally, the transducer 10 can be machined down to a desired diameter and a ground electrode can be evaporated onto a front face of the transducer. The desired diameter of the transducer, in one exemplary aspect, can be between 1 and 10 mm. In a further exemplary aspect, the desires diameter of the transducer can be about 3 mm.

Figure 3B:
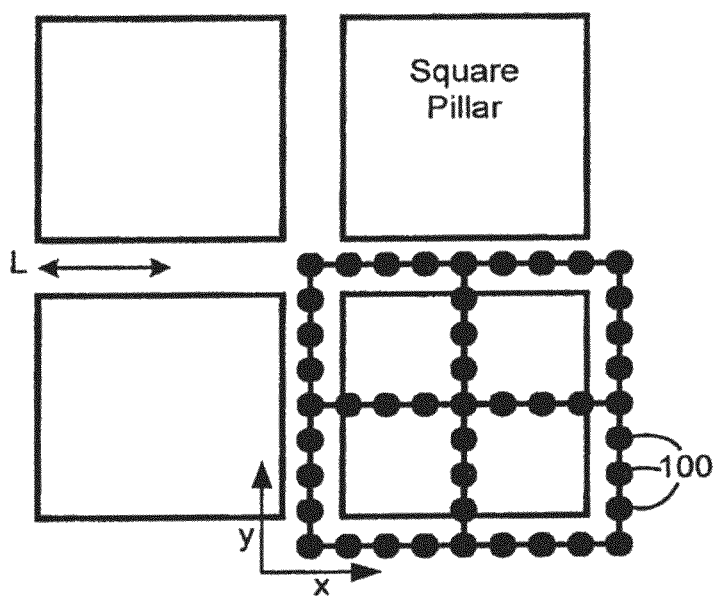
FIG. 3B is an enlarged top elevational view of a conventional, prior art transducer with square cross-sectional shaped pillars.
Figure 3C:
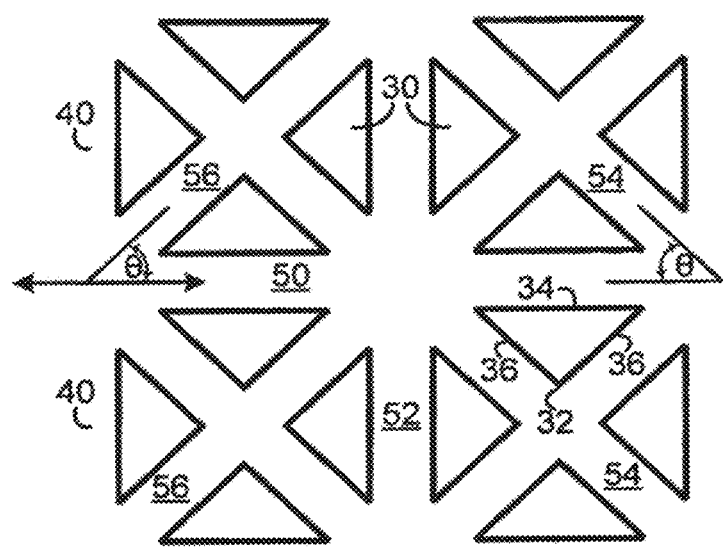
FIG. 3C is an enlarged top elevational view of an alternative embodiment of the transducer with triangular cross-sectional shaped pillars.

In other embodiments and as shown in FIG. 3C, the transducer 10 of the current application can comprise a plurality of pillars 30 for emitting energy in response to an input signal. The plurality of pillars can be positioned in adjacent, substantially parallel rows, wherein each pillar has a substantially triangular cross-sectional shape for suppressing the lateral modes at the operating frequencies. Each pillar can have an apex 32, an opposed base 34 having opposed edges, and a pair of side walls 36 that extend from the apex to the respective edges of the base. In this aspect, the plurality of pillars can comprise of a plurality of paired pillars, wherein each of the paired pillars comprises a first pillar 42 positioned adjacent to a second pillar 44 such that the base of the first pillar is spaced from and substantially opposes the base of the second pillar. Further, each row of the array of pillars can comprise a plurality of paired pillars that are positioned adjacent each other such that one side wall of the first pillar is spaced from and substantially opposes one side wall of the second pillar.

In this exemplary embodiment, the transducer can further comprise a substrate 20 that is at least partially curved. It is contemplated that the substrate and the plurality of pillars can form an electrically monolithic structure, which is configured for emitting energy in response to the input signal. The array of pillars can define a plurality of first troughs 50 extending substantially parallel to a longitudinal axis of the substrate, a plurality of second troughs 52 extending substantially transverse to the longitudinal axis of the substrate, and a plurality of third troughs 54 extending at an acute angle $\theta$ relative to the longitudinal axis of the substrate. In one aspect, the width of the respective first, second, and third troughs can be substantially equal. In another aspect, at least a portion of the respective first, second, and third troughs can be at least partially filled with a fill material.

In another embodiment, the transducer 10 of the current application can comprise a substrate 20 having a longitudinal axis, a plurality of pillars 30 extending outwardly therefrom the substrate, and a means for suppressing the lateral modes of the transducer at higher operating frequencies, such as, at or above 15 MHz, at or above 20 MHz, or at or above 30 MHz. In one aspect, at least a portion of the substrate 20 can be flexible. In another aspect, at least a portion of the substrate can be curved in cross-section such that the transducer is geometrically curved. In yet another aspect, the substrate and the plurality of pillars 30 can be formed from a single-crystal piezoelectric or from a piezoelectric material such as for example lead zirconate titanate.

In yet another aspect, the plurality of pillars can form an array of pillars positioned in adjacent rows 40, wherein each row of the array of pillars extends substantially parallel to the longitudinal axis of the substrate. In yet another aspect, the means for suppressing the lateral modes can comprise each pillar 30 having a triangular cross-sectional shape that has an apex 32, an opposed base 34 having opposed edges, and a pair of side walls 36 that extend from the apex to the respective edges of the base. In one example, the array of pillars can define a plurality of first troughs 50 extending substantially parallel to the longitudinal axis of the substrate, a plurality of second troughs 52 extending substantially transverse to the longitudinal axis of the substrate, a plurality of third troughs 54 extending at about an acute angle $\theta$ relative to the longitudinal axis of the substrate, such as, for example and not meant to be limiting, a 45° angle. Optionally, a plurality of fourth troughs 56 can be formed that each extends substantially transverse to the third troughs.

In this embodiment, in one aspect, the width of the first trough can be substantially the same as the width of the second trough. In another aspect, the width of the second trough 52 can be substantially the same as the width of the third trough. In a finisher aspect, the width of the third trough can be substantially the same as the width of the fourth trough. In yet another aspect, at least a portion of the respective first, second, third, and fourth troughs can be at least partially filled with a fill material 22. The fill material can comprise, for example, a polymeric material, such as, for example, loaded epoxy, polymer micro-spheres, crystal bond, photoresist material and the like, as is customary and standard practice in the manufacture of composite transducers, or they may be left, at least in part, unfilled. In one exemplary aspect, the fill material can be, for example and without limitation, SU8 photoresist, PZT powder, and the like.

In yet another embodiment, a method of producing an ultrasonic wave emission pattern at higher operating frequencies, such as, at or above 15 MHz, at or above 20 MHz, or at or above 30 MHz, is provided. In one aspect, the method can comprise applying an electric signal to a piezoelectric substrate of a transducer 10 having a plurality of pillars 30 extending outwardly therefrom the substrate 20. The lateral modes of the transducer can be suppressed by providing each pillar 30 with a triangular cross-sectional, shape that has an apex 32, an opposed base 34 having opposed edges, and a pair of side walls 36 that extend from the apex to the respective edges of the base. In one aspect, the array of pillars can comprise a plurality of paired pillars, wherein each of the paired pillars comprises a first pillar 42 positioned adjacent to a second pillar 44 such that the base of the first pillar is spaced from and substantially opposes the base 34 of the second pillar. In another aspect, each row 40 of the array of pillars can comprise a plurality of paired pillars that are positioned adjacent each other such that one side wall of the that pillar is spaced from and substantially opposes one side wall 36 of the second pillar.

In this embodiment, the array of pillars can define a plurality of first troughs 50 extending substantially parallel to a longitudinal axis of the substrate, a plurality of second troughs 52 extending substantially transverse to the longitudinal axis of the substrate, and a plurality of third troughs 54 extending at an acute angle $\theta$ relative to the longitudinal axis of the substrate. In one aspect, the width of the respective first, second and third troughs can be substantially equal. In another aspect, at least a portion of the respective first, second, and third troughs can be at least partially filled with a fill material. In yet another aspect, the substrate can be flexible.

In use, in one aspect, the transducer 10 is configured, at higher operating frequencies, such as, at or above 15 MHz, at or above 20 MHz, or at or above 30 MHz, can spread the lateral energy out over a broad spectrum of frequencies. At these higher operating frequencies, the triangular cross-sectional shape of the plurality of pillars 30 can remove or suppress virtually all of the lateral modes within the individual pillars and can break up the pillar-to-pillar periodicities that can cause spurious modes. Further, the spread in lateral energy can also help to rapidly dampen secondary ringing in the thickness mode.

Example

In order to demonstrate the efficacy of the transducer described herein, two sample transducers were prepared and tested, as described below. Example 1 was a transducer having a plurality of pillars having a triangular cross-sectional shape, as described herein. The triangular pillars were isosceles in shape and arranged in the pattern shown in FIG. 3A. Example 2 was a transducer having a plurality of pillars having a square cross-sectional shape, as is blown in the art, and as shown in FIG. 3B. Each composite structure had 15 μm, troughs, a 42 μm pillar height, and a fill material volume fraction of approximately 25%. FIGS. 3A and 3D show the arrangement of both composite structures as well as identifying different points on the exemplary transducers that were closely analyzed.

Figure 4A:
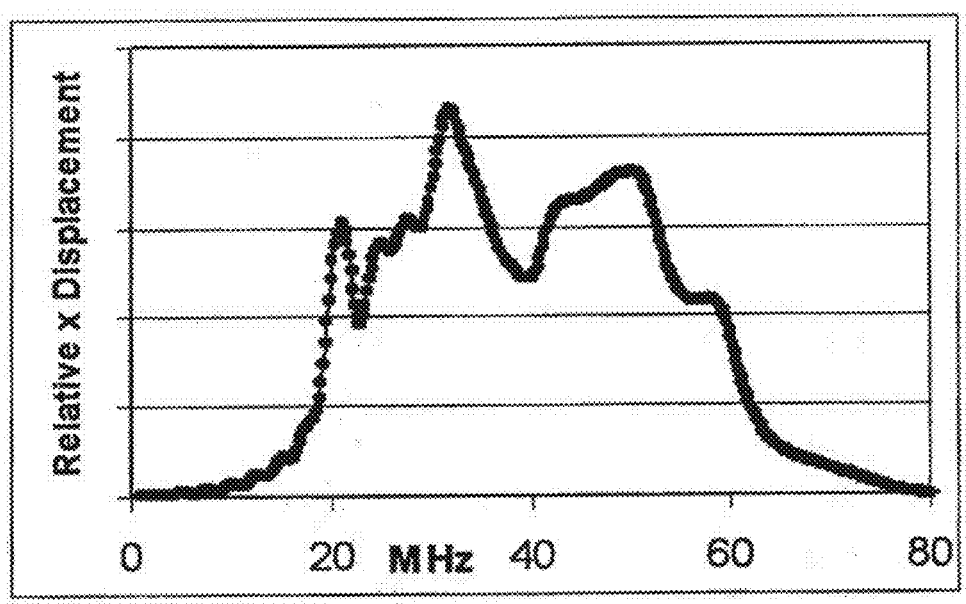
FIG. 4A is a chart showing the sum of the lateral displacement spectra of all points labelled on the transducer of FIG. 3A with triangular cross-sectional shaped pillars.
Figure 4B:
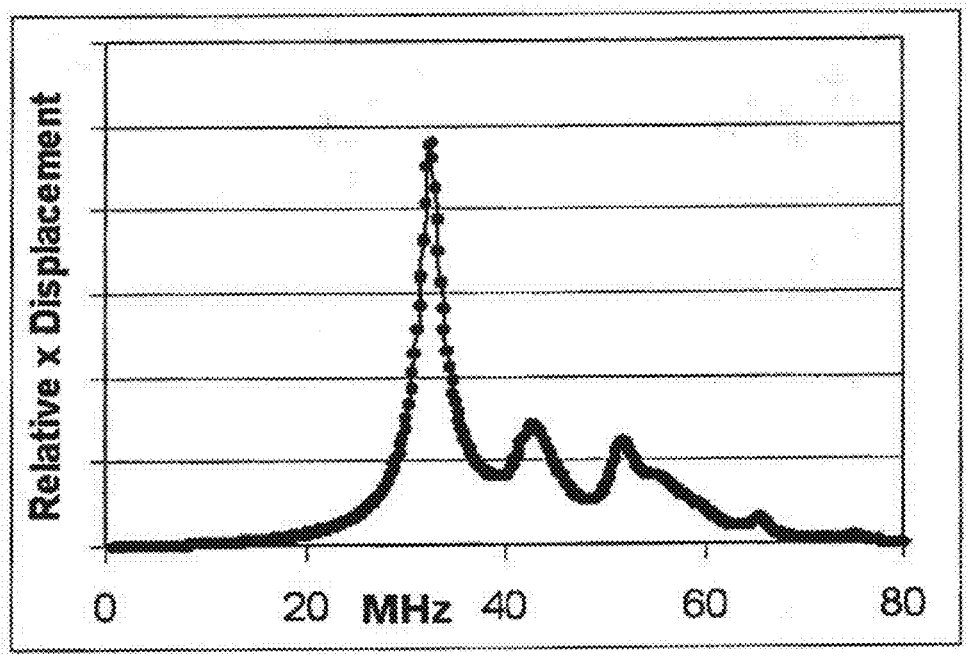
FIG. 4B is a chart showing the sum of the lateral displacement spectra of all points labelled on the conventional transducer of FIG. 3B with square cross-sectional shaped pillars.

For each point marked on the respective FIGS. 3A and 3B, the displacements were simulated in all three dimensions when excited with a monocycle excitation pulse in the thickness dimension. To analyze the lateral modes, the displacements 100 for each point were summed in the frequency domain. FIGS. 4A and 4B show the displacements 100 summed together for the x direction. As can be seen in FIGS. 4A and 4B, the square-pillar composite design (FIG. 4B) possesses lateral displacements in much narrower bands than the triangular-pillar composite (FIG. 4A).

Figure 5A:
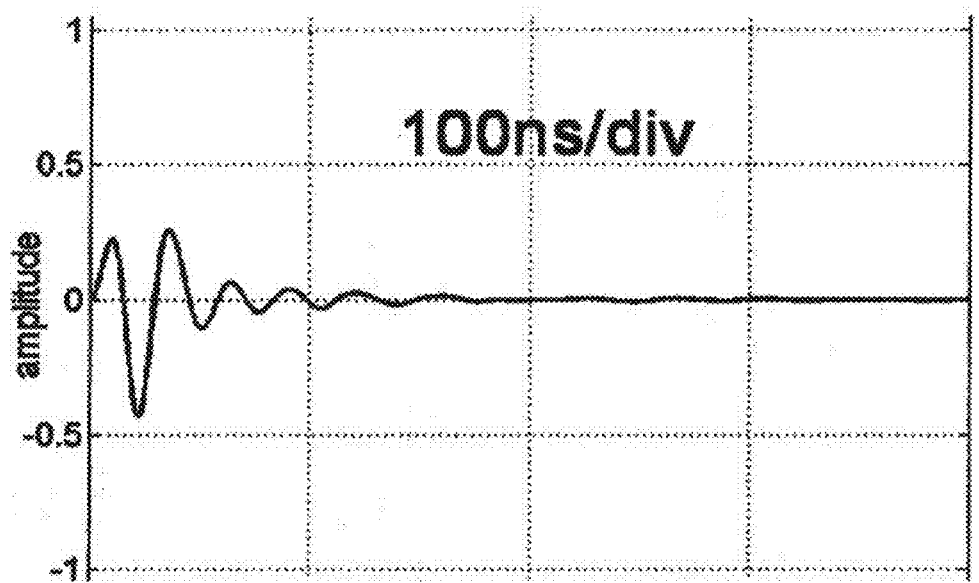
FIG. 5A is a chart showing the simulated one-way pulse responses using PZFlex for an exemplary triangular cross-sectional shaped pillar.
Figure 5B:
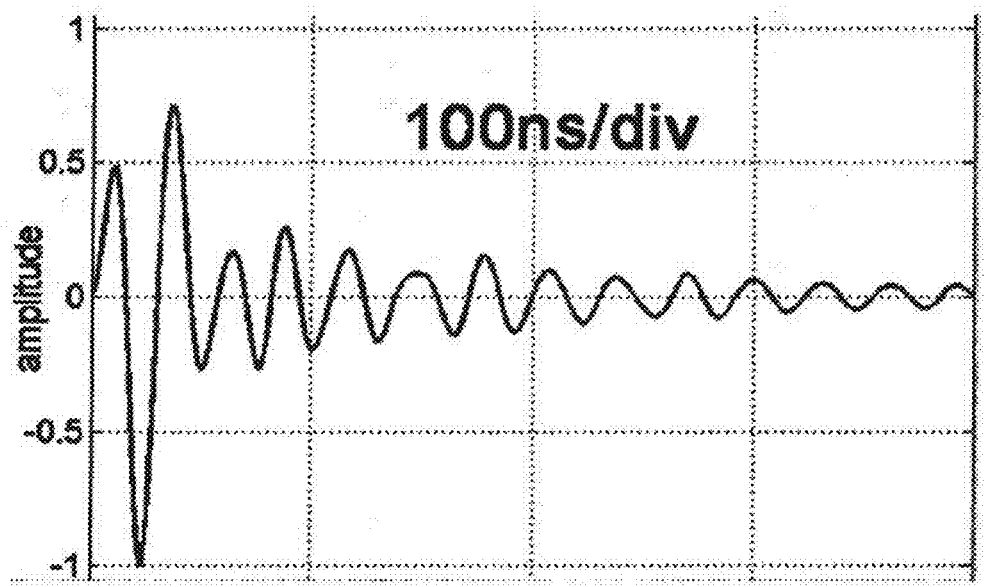
FIG. 5B is a chart showing the simulated one-way pulse responses using PZFlex for an exemplary conventional square cross-sectional shaped pillar.
Figure 6A:
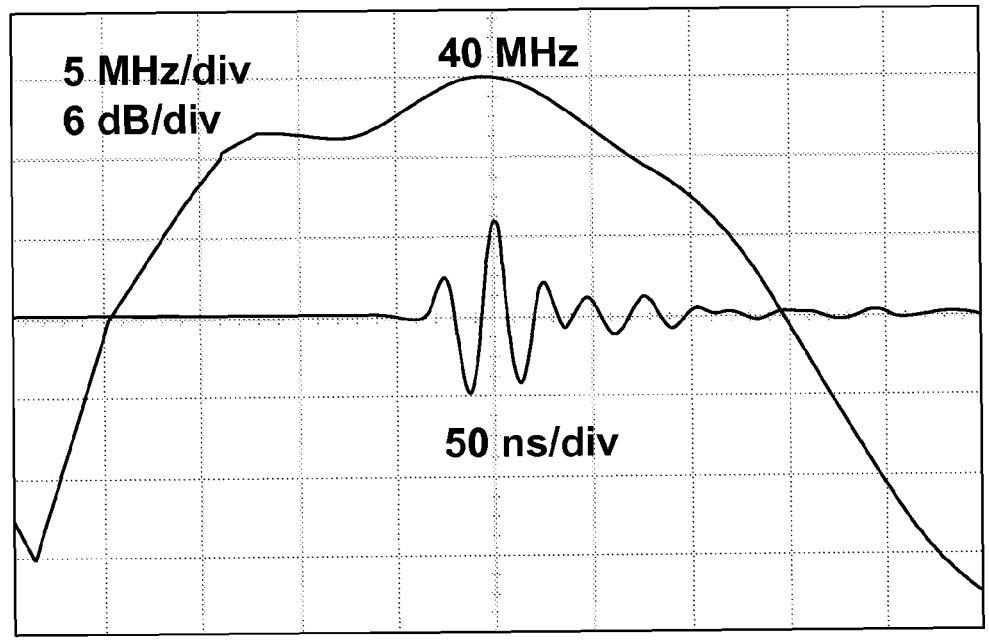
FIG. 6A is a chart showing the simulated two-way pulse-echo responses using PZFlex for an exemplary triangular cross-sectional shaped pillar.
Figure 6B:
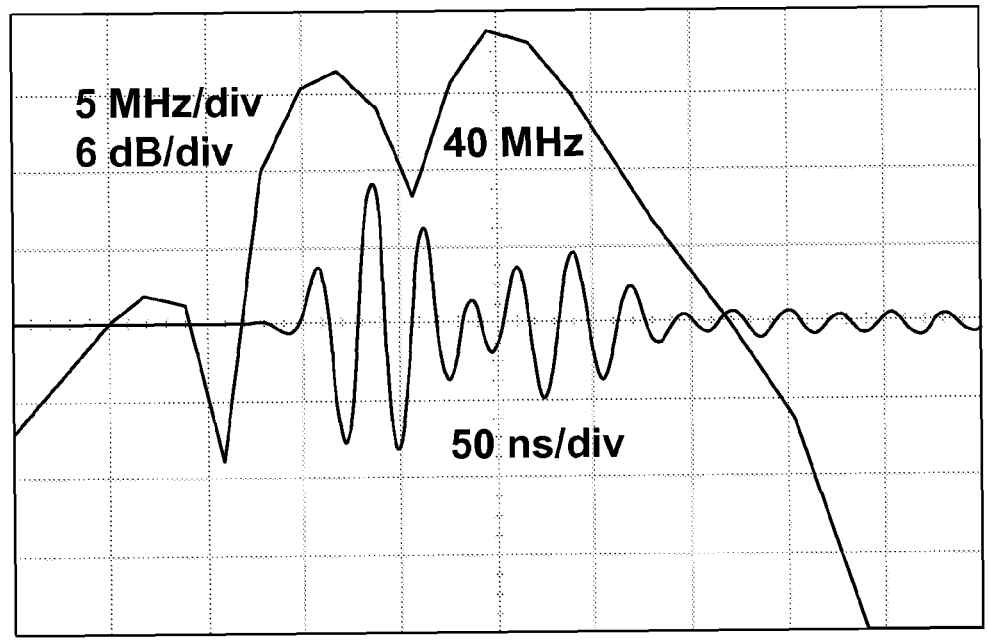
FIG. 6B is a chart showing the simulated two-way pulse-echo responses using PZFlex for an exemplary conventional square cross-sectional shaped pillar.
Figure 7:
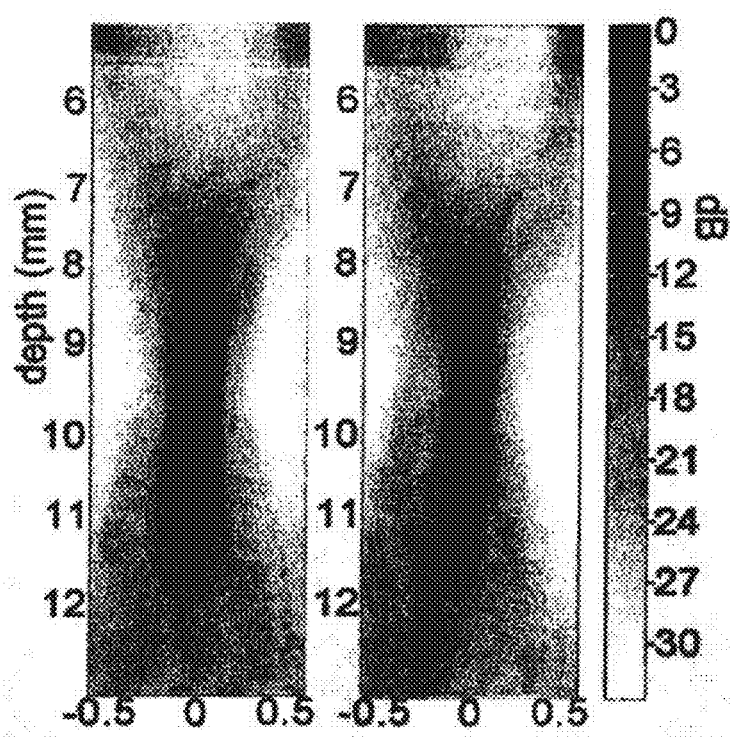
FIG. 7 is an image of a one-way measured radiation pattern for an exemplary triangular cross-sectional shaped pillar.
Figure 8:
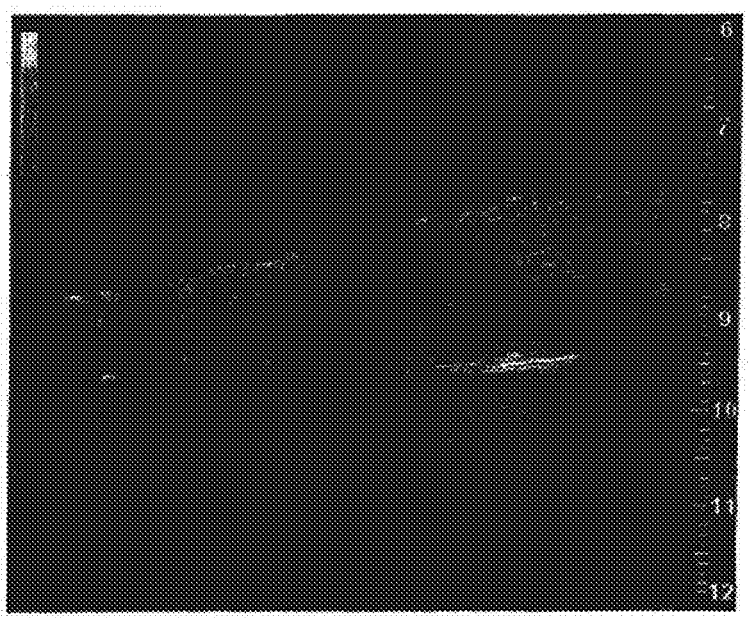
FIG. 8 is an image of a human finger generated with an exemplary transducer having a plurality of triangular cross-sectional shaped pillars thereon.

To evaluate the performance of both transducers, the following characteristics were measured: electrical impedance, pulse-echo response, and one-way radiation pattern. The electrical impedance magnitude at 40 MHz was measured to be 9 ohms for the square-pillar composite and 11 ohms for the triangular cross-sectional shaped pillar composite. The −6 dB pulse echo bandwidths were measured to be 20% for the square-pillar composite and 55% for triangular cross-sectional shaped pillar composite. The pulses are shown in the form of oscilloscope screen captures in FIGS. 5A and 5B. The pulse echoes were generated by situating a quartz flat in front of the transducers at the geometric focus. The pulse amplitude for the square-pillar composite was measured to be 5.5 dB more sensitive than the triangular cross-sectional shaped pillar composite. The peak insertion losses of the two composites were measured to be approximately −25 dB for the square-pillar and −31 dB for the triangular cross-sectional shaped pillar composite. The one-way radiation pattern for the triangular cross-sectional shaped pillar composite was then measured by scanning a needle hydrophone in from of the transducer in all three dimensions. FIG. 7 shows the resulting radiation pattern in two perpendicular planes (x, y planes). The average −3 dB beamwidth was measured to be 120 μm and the −3 dB depth-of-field was measured to be 2.5 mm.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A transducer, comprising:
a transducer substrate having a longitudinal axis, wherein the substrate is configured to operate at ultrasound frequencies at or above 15 MHz; and
a rectangular array of groups of pillars extending outwardly from the substrate, wherein the groups are arranged in adjacent rows that extend substantially parallel to the longitudinal axis, wherein each group includes at least first and second pillars having a triangular cross-section, and wherein the first and second pillars are separated by a first kerf oriented at a first angle not parallel or perpendicular to the longitudinal axis of the substrate.

2. The transducer of claim 1 wherein the groups of pillars are separated by a plurality of second kerfs and third kerfs, wherein the second kerfs are substantially perpendicular to the third kerfs.

3. The transducer of claim 2 wherein a width of the first kerf is substantially the same as a width of the second kerf.

4. The transducer of claim 2 wherein at least a portion of the first kerfs, the second kerfs, or the third kerfs is at least partially filled with a fill material.

5. The transducer of claim 4 wherein the fill material is a loaded epoxy.

6. The transducer of claim 4 wherein the fill material is a photoresist material.

7. The transducer of claim 1 wherein the substrate is flexible.

8. The transducer of claim 1 wherein the substrate is curved in cross-section such that the transducer is geometrically curved.

9. The transducer of claim 1 wherein the substrate and the groups of pillars is formed from a piezoelectric material.

10. The transducer of claim 9 wherein the piezoelectric material is lead zirconate titanate.

11. The transducer of claim 1 wherein the first angle is 45 degrees.

12. A transducer, comprising:
a piezoelectric substrate having a longitudinal axis; and
a rectangular array of groups of pillars extending outwardly from the substrate, wherein each group includes a first pillar and at least a second pillar, wherein the first and second pillars are separated by a first kerf oriented at a first angle not parallel or perpendicular to the longitudinal axis of the substrate, wherein the groups of pillars are separated by second kerfs and third kerfs, and wherein the second kerfs are substantially perpendicular to the third kerfs.

13. The transducer of claim 12 wherein the first pillar and the second pillar have a triangular cross-section.

14. The transducer at claim 13 wherein at least a portion of the first kerfs, the second kerfs, or the third kerfs is at least partially filled with a fill material.

15. The transducer of claim 14 wherein the fill material is a loaded epoxy.

16. The transducer of claim 14 wherein the fill material is a photoresist material.

17. The transducer of claim 12 wherein the each group of pillars has a rectangular outer perimeter.

18. The transducer of claim 12 wherein the groups of pillars are configured to suppress lateral modes at transducer operating frequencies of at least 15 MHz.

19. The transducer of claim 12 wherein each pillar has a polygonal shape with an odd number of sides.

20. The transducer of claim 2 wherein the second kerfs are parallel to the longitudinal axis, and wherein the third kerfs are perpendicular to the longitudinal axis.

21. A high-frequency ultrasound transducer, comprising:
a transducer substrate having a longitudinal axis; and
an array of groups of pillars extending outwardly from the substrate, wherein each group includes a first pillar and at least a second pillar, wherein the first and second pillars are separated by a first kerf oriented at a first angle not parallel or perpendicular to the longitudinal axis of the substrate, wherein each pillar has a base and an apex, and wherein a distance between the base and the apex ranges from between about 5 microns to about 70 microns.

* * * * *